(12) United States Patent
Pandya

(10) Patent No.: US 6,589,555 B2
(45) Date of Patent: Jul. 8, 2003

(54) EFFERVESCENT VITACEUTICAL COMPOSITIONS AND RELATED METHODS

(76) Inventor: Mahendra Pandya, 8018 Daytona St. NW., Massillon, OH (US) 44646-2336

(*) Notice: Subject to any disclaimer, the term of this patent is extended or adjusted under 35 U.S.C. 154(b) by 0 days.

(21) Appl. No.: 09/749,304

(22) Filed: Dec. 27, 2000

(65) Prior Publication Data

US 2001/0051134 A1 Dec. 13, 2001

Related U.S. Application Data

(60) Provisional application No. 60/173,431, filed on Dec. 29, 1999.

(51) Int. Cl.$^7$ .............................................. A61K 9/46
(52) U.S. Cl. ....................................................... 424/466
(58) Field of Search .............................. 424/466, 489, 424/465

(56) References Cited

U.S. PATENT DOCUMENTS

| | | | |
|---|---|---|---|
| 3,495,001 A | | 2/1970 | Leonards |
| 3,518,344 A | | 6/1970 | Welsh et al. |
| 4,083,950 A | | 4/1978 | Duvall et al. |
| 4,650,669 A | * | 3/1987 | Alexander et al. ............ 424/44 |
| 4,783,331 A | | 11/1988 | Alexander et al. |
| 4,942,036 A | | 7/1990 | Geho et al. |
| 5,543,153 A | * | 8/1996 | Walton ........................ 424/466 |
| 5,762,951 A | * | 6/1998 | Maasz et al. ................ 424/439 |
| 5,824,339 A | | 10/1998 | Shimizu et al. |
| 5,834,019 A | | 11/1998 | Gergely et al. |
| 5,837,286 A | | 11/1998 | Pandya et al. |
| 5,869,095 A | | 2/1999 | Gergely et al. |
| 5,912,012 A | | 6/1999 | Carlin et al. |
| 5,919,483 A | | 7/1999 | Takaichi et al. |
| 5,962,022 A | | 10/1999 | Bolt et al. |

FOREIGN PATENT DOCUMENTS

WO    B1 WO 01/01992 A1    1/2001

OTHER PUBLICATIONS

Derwent Acc No.: 2001–138059, Maier, Jan. 2001.*

* cited by examiner

*Primary Examiner*—James M. Spear
(74) *Attorney, Agent, or Firm*—Wolf, Greenfield & Sacks P.C.

(57) ABSTRACT

The invention relates to a dry effervescent composition containing inulin, and optionally containing at least one vitaceutical and other active agents. The effervescent products optionally contain lubricants and essential oils and can generate magnesium malate, a therapeutic effector. The invention also relates to a dry effervescent composition containing glucosamine. The invention also encompasses methods of preparing the effervescent compositions of the invention.

28 Claims, No Drawings

EFFERVESCENT VITACEUTICAL COMPOSITIONS AND RELATED METHODS

RELATED APPLICATION INFORMATION

This application claims the benefit of priority under 35 USC 119 to U.S. Provisional Patent Application No. 60/173,431 filed on Dec. 29, 1999 and entitled Effervescent Vitaceutical Compositions and Related Methods. The entire contents of the provisional patent application are hereby incorporated by reference.

FIELD OF THE INVENTION

The invention relates to a dry effervescent composition containing at least one vitaceutical, and optionally containing inulin and other active agents. The effervescent products optionally contain lubricants and essential oils and can generate magnesium malate, a therapeutic effector. The invention also encompasses methods of preparing the effervescent compositions of the invention.

BACKGROUND OF THE INVENTION

Many types of formulations are available for administering medicaments to a subject. Solid dosage forms which are swallowed, such as tablets and capsules are useful because they provide quick and easy administration routes as well as accurate dosages. Many medicinal compositions, including vitamins, nutritional supplements and medicines have unpleasant tastes. These compositions can be administered in the form of a tablet or capsule to avoid unpleasant taste. Solid dosage forms, however, must disintegrate in the gastrointestinal tract and the medicament must dissolve before it is absorbed. As a result, absorption tends to be slower than from a liquid suspension and may be incomplete. Additionally, some subjects have difficulty swallowing tablets and capsules. Another draw-back of solid dosage forms is that tablets and capsules can only have a maximal size which can easily be swallowed and thus the dosage cannot be increased above that size. If more medicament is required, multiple tablets or capsules must be administered.

Medicinals can also be administered as liquids, chewables or formulations which dissolve in the mouth. In these instances, it is desirable to add a component which masks the taste of the bitter medicinals. Fruit flavoring mixed with sugars are often used.

Soluble medicaments administered in aqueous suspensions can also be used for administering medicaments. Aqueous suspensions are useful because they provide good bio-availability of the medicament. These preparations, however, often have limited shelf-life and it is difficult to accurately measure the dose of a medicament being provided. It is also difficult to mask the bitter taste of medicaments in this type of formulation.

In order to avoid some of the problems associated with administration of medicaments in the forms of solid dosages or aqueous suspensions, effervescent formulations can be used. Effervescent formulations usually require components which mask the taste because these formulations are dissolved in water prior to ingestion. Some effervescent formulations have been prepared using citrus flavoring. Other taste-masking substances include clove oil with a supportive flavor component or calcium carbonate, such as those described in U.S. Pat. No. 5,837,286. Clove oil is capable of masking the bitter taste of medicinals, particularly analgesics, expectorants, anti-tussives, decongestants or combinations thereof.

Effervescent formulations are well-known to those of ordinary skill in the art. These formulations include those described in U.S. Pat. Nos. 3,495,001; 3,518,344; 4,083,950; 4,783,331; 4,942,039; 5,824,339; 5,834,019; 5,962,022; 5,919,483; 5,912,012, and 5,869,095, the entire contents of which are hereby incorporated by reference. In general, effervescent formulations include an acid/base component such as edible organic acids such as citric acid and a carbonate or bicarbonate, lubricants, sweeteners, excipients, clarity-enhancing components, surfactants, emulsifiers, sorbitol, and mannitol to enhance compressibility.

When the effervescent formulation is dissolved in water, the base liberates carbon dioxide to produce the effervescent or fizzy characteristics of the formulation. The use of effervescent formulations to administer medicaments provides the advantage that disintegration of the medicament in the gastrointestinal tract is accomplished easily. Some of the disadvantages of prior art effervescent formulations include a difficulty with maintaining stability of hydrophobic compounds, the bad taste associated with certain medicaments, and the quick time with which the effervescent formulation must be consumed once it is mixed with water.

Another problem associated with the use of effervescent compositions has been the inability to incorporate acid-sensitive drugs because these compositions will hydrolyze or decompose while in contact with the acid of the effervescent system. Thus, these compositions are not stable for reasonable periods of time. Additionally, hydrophobic particles within the drug contained within the effervescent composition tend to leach out of the effervescent composition when it is mixed with water and deposit along the bottom or sides of the glass. Loratadine is an example of a hydrophobic active agent which is difficult to formulate in an effervescent composition.

Additionally, effervescent compositions are not a preferred composition for formulating hygroscopic medicaments. Hygroscopic medicaments take up and absorb moisture. When hygroscopic compounds in effervescent formulations are exposed to moisture they are quickly inactivated.

SUMMARY OF THE INVENTION

The invention is directed to effervescent compositions having improved properties. One of the effervescent compositions of the inventions is an effervescent formulation containing an inulin. The inulin increases the effervescence time, which would allow a subject to ingest the effervescent drink over a longer period of time. This would allow the subject to drink the effervescent formulation in a relaxed manner as a regular drink. Thus, one aim of the formulations of the invention, is to provide a composition which can be enjoyed in the form of a drink which tastes good and is enjoyable. This drink overcomes the difficulty associated with other forms of administering medicine, such as reluctance to swallow pills, bad taste associated with medicaments, and general problems associated with inconvenience due to the frequency and quantity of taking pills. Additionally, it is desirable to maintain intestinal health for maximal nutrient absorption and assimilation. Inulin can help to improve and maintain intestinal health, reducing stomach distress, increasing mineral absorption, helping to multiply the native gut microorganisms and decreasing pathogenic bacteria in the gut to promote nutrient assimilation.

The invention in other aspects relates to an effervescent formulation which produces a therapeutic agent when mixed with water. Thus the therapeutic agent is formed "in situ." The effervescent compositions, according to this aspect of the invention, are capable of generating magnesium malate which has a therapeutic effect in the treatment of muscle soreness and has been used to promote muscle relaxation. In other aspects, the invention relates to methods of treating or preventing muscle soreness and/or promoting muscle relaxation by administering an effervescent composition of the invention.

According to yet another aspect of the invention, an effervescent composition containing a hygroscopic compound such as glucosamine is provided. Glucosamine is an active agent which has been used for the treatment of osteoarthritis. Because glucosamine is hygroscopic and oxidizes when exposed to air for long periods of time, it is predominantly available in hard gelatin capsule forms. Some tablet forms are also available. The tablets, however, suffer from deterioration due to moisture and oxygen. The novel effervescent formulations of the invention containing glucosamine and or other hygroscopic compounds are useful for delivering glucosamine for therapeutic purposes because they contain ingredients which help prevent the oxidation and deterioration of glucosamine within the formulation. The effervescent formulations include ascorbic acid which selectively protects glucosamine against oxidation by preferentially being oxidized. The formulation also contains sorbitol and/or inulin, which because they are more hygroscopic than glucosamine, selectively protect the glucosamine against moisture. Additionally, some of the most common side-effects of glucosamine are stomach distress, diarrhea, and nausea. Prebiotic inulin help to calm the gastrointestinal tract, thus minimizing the side-effects of glucosamine.

In another aspect, the invention is an effervescent formula which includes lubricants such as micronized fumaric and adipic acid without any additional lubricants. These compounds when used in a micronized form have the advantage that they develop lubricant properties. These compounds are usually used in effervescent formulations in combination with additional lubricants. When micronized fumaric acid or adipic acid are used according to the invention as the sole lubricant in the formulation.

The invention in other aspects relates to improved effervescent formulations including lubricants composed of vegetable oils flavored with essential oils such as orange, lemon, lime, etc. One problem associated with the effervescent formulations of the prior art is that when vegetable oils are used as lubricants, the vegetable oil floats to the top of the effervescent solution. Because the vegetable oil is on top it is the first part of the solution that is tasted. Many vegetable oils such as cotton seed oil which are good lubricants have an unpalatable flavor. The formulations of the invention include an essential oil mixed in to the vegetable oil. It was discovered according to the invention that the essential oils were completely capable of masking the unpleasant taste of the vegetable oil.

Thus, the invention in one aspect relates to an effervescent composition including a basic effervescent component; at least one pH neutralizing agent; and an inulin. In preferred embodiments the basic effervescent component is a carbonate or bicarbonate selected from the group consisting of sodium and/or potassium hydrogen carbonates and bicarbonates, calcium carbonate, magnesium carbonate, and amino acid carbonates. In other preferred embodiments the pH neutralizing agent is selected from the group consisting of L-tartaric acid, citric acid, lactic acid, malic acid, fumaric acid, aspartic acid, ascorbic acid, and amino acids.

In some embodiments the effervescent composition includes a vitaceutical, e.g., a vitamin, a mineral, an antioxidant, a nutraceutical etc. In some preferred embodiments the carbonate or bicarbonate is selected from the group consisting of magnesium carbonate and calcium carbonate and the pH neutralizing agent is malic acid. In other preferred embodiments the composition includes a hygroscopic compound such as glucosamine.

In other embodiments the effervescent compositions include a lubricant such as a micronized fumaric acid or adipic acid or a vegetable oil flavored with an essential oil such as orange, lemon, lime, etc.

The composition may also include other additives. For instance, in some embodiments the effervescent composition includes at least one sweetener, wherein the sweetener is selected from the group consisting of stevia, fructose, ribose, sucrose, tagatose, sucralose, malitol, erythritol, zylitol, acesulfame potassium, aspartame, and saccharine. In other embodiments the effervescent composition includes an excipient, a surfactant, an emulsifier, an osmotic pressure-regulator, and/or an electrolyte.

In other preferred embodiments the effervescent composition is composed of a carbonate or bicarbonate of sodium and potassium, citric acid, and inulin. In other embodiments effervescent composition is composed of magnesium carbonate, malic acid, and inulin.

In other preferred embodiments the effervescent composition include magnesium malate, riboflavin-5-phosphate, calcium pentothenate, peroxidine HCL boron chelate, copper gluconate, manganese gluconate, zinc sulfate, ascorbic acid and/or vitamin E.

According to another aspect the invention is an effervescent composition. The composition includes a basic effervescent agent; at least one pH neutralizing agent; and glucosamine. In one embodiment the composition also includes inulin and/or a vitaceutical.

In other aspects the invention is a method for treating or preventing muscle soreness. The method includes the steps of administering to a subject an effervescent composition of the invention, which produces magnesium malate in situ, in order to prevent or treat muscle soreness in a subject. The effervescent composition includes magnesium carbonate and malic acid which produce magnesium malate in situ.

In other aspects the invention is a method for treating or preventing osteoporosis. The method includes the steps of administering to a subject an effervescent composition of the invention, which produces calcium citrate in situ, in order to prevent or treat osteoporosis in a subject. The effervescent composition includes calcium carbonate and citric acid which produce calcium citrate in situ.

Each of the limitations of the invention can encompass various embodiments of the invention. It is, therefore, anticipated that each of the limitations of the invention involving any one element or combinations of elements can be included in each aspect of the invention.

DETAILED DESCRIPTION

The effervescent formulations of the invention overcome several of the prior art problems and provide a desirable way for administering medicaments. For example the effervescent compositions of the invention are particularly suitable for administering medicaments which are bitter tasting or otherwise have a negative flavor, because the formulations of the invention are capable of masking the flavor, such that the final formulation has a desirable taste. Bitter tasting medicaments include, but are not limited to, β-lactam antibiotics, including penicillins, such as amoxycillin or ampicillin, optionally, mixed with a β-lactamase inhibitor; antihistamine $H_2$-receptor antagonists, anti-ulcer compounds such as cimetidine, non-steroidal anti-inflammatory agent such as nabumetone, and bile acid sequestrants.

Another advantage of the invention is that the effervescent formulations can be used to administer hygroscopic agents, preferably glucosamine. It was discovered that a stable effervescent formulation containing glucosamine could be generated even though glucosamine is hygroscopic. In one aspect of the invention an inactive hygroscopic component is mixed into the glucosamine effervescent formulation, to provide increased stability of the glucosamine. Inactive hygroscopic agents include but are not limited to mannitol, sorbitol and inulin, which are considerably more hygroscopic than glucosamine. As a result, their presence in the effervescent formulation selectively protects the glucosamine from the damaging effects of moisture. In some embodiments, the effervescent formulation also includes ascorbic acid which helps to protect the glucosamine from oxidation. The ascorbic acid preferentially will be oxidized, preventing oxidation of the active agent.

As discussed above, the preferred effervescent formulations of the invention contain inulin. Inulins are a well known class of compounds which include disaccharides, polysaccharides or oligosaccharides, such as fructooligosaccharides. Inulins have a variety of desirable properties such as the ability to increase the effervescence time, which allows a subject to ingest the effervescent drink over a longer period of time. Additionally, inulins help to improve and maintain intestinal health, reducing stomach distress, increasing mineral absorption, helping to multiply the native gut microorganisms and decreasing pathogenic bacteria in the gut to promote nutrient assimilation. Inulins are commercially available from a variety of sources such as, for example, Inulin IQ, Inulin HD, and Inulin EXL from Imperial Sensun, Sugarland TX, beflora plus, and Triacho from NJ as well as generics.

The effervescent formulations of the invention can be used by anyone in order to ingest vitaceuticals or nutraceuticals. These compositions may be particularly preferred for use by athletes, hikers, travelers, etc. because they can be administered as refreshing drinks. As described above, some of the formulations produce effervescence for an extended period of time, lasting 5 or preferably 10 minutes or more. This is advantageous because it is capable of producing a drink with carbonation that can be conveniently stored and carried in a tablet form and mixed with water at time of consumption. Some of these formulations are also convenient for this class of subjects because the effervescent formulation produces magnesium malate which soothes muscle soreness and induces muscle relaxation. Thus, in addition to providing a refreshing beverage and administering necessary vitaceuticals and nutraceuticals, the effervescent formulations of the invention also are capable of providing a natural compound which helps to prevent and treat muscle soreness. As used herein the term "prevent" refers to inhibiting completely or partially muscle soreness.

Most effervescent formulations include three main components, a shell and/or binding agent, an acidic effervescent component, referred to herein as a pH neutralizing agent and a basic effervescent component. The shell and/or binding agent is generally composed of sugars (lactose, glucose) sorbitol, zylitol, and mannitol. Other additives include sweetening agents such as sugars, saccharine, sodium cyclamate and aspartame; flavoring and aroma agents; lubricating agents such as polyethylene glycose, silicone oils, stearates, cotton seed or canola oil, and adipic acid.

As mentioned above, the effervescent component includes both basic and acidic ingredients. The basic ingredient causes liberation of carbon dioxide when it and the acid component are contacted with water. Typical basic effervescent components include but are not limited to sodium hydrogen carbonate and a carbonate or bicarbonate such as sodium bicarbonate sodium carbonate, and magnesium carbonate, ammonium carbonate, or other physiologically-acceptable alkaline earth metal carbonate mixtures such as potassium or calcium (bi)carbonate or sodium glycine carbonate. pH neutralizing agents include but are not limited to edible organic acids such as hydroxycarboxylic acids including citric acid, tartaric acid, malic acid, lactic acid, gluconic acid, saturated aliphatic carboxylic acid such as acetic acid, succinic acid and unsaturated aliphatic carboxylic acid such as fumaric acid, and adipic acid. In general, the acidic component is present within the powder formulation in a range of approximately 0.5–50% or, more preferably, 1.5–30% of the weight of the composition. The basic component is generally present in a range of 0.5–50% or more preferably, 1.5–30% of the weight of the composition.

When the effervescent composition is formulated as a tablet, it is preferred that lubricants are included in the mixture to aid in the compression process. Lubricants must not interfere with the flowability or compressibility of the formulation or the release of the active agent. Standard lubricants used in preparing tablets include hydrophobic lubricants such as, for example, calcium stearate, magnesium stearate, talc, and vegetable oils; water-soluble lubricants such as, for example, fumaric acid, adipic acid, boric acid, sodium benzoate, potassium benzoate, sodium propionate, sodium stearyl fumarate, sodium lauryl sulfate, magnesium lauryl sulfate, L-leucine, and various polyethylene glycols, calcium sorbate, and potassium sorbate. Other common lubricants include, for instance, compritol, HD5-ATO available from Gattefosse (Westwood, N.J.) and fumaric acid. In general, it is preferred that the water soluble lubricants be used for the preparation of effervescent compositions because they avoid the problems associated with hydrophobic lubricants, such as the production of a residue or film, which can trap the active ingredients, preventing the delivery of all of the active ingredients. In general, lubricants are provided in approximately 0.5–5% by weight of the composition.

The effervescent compositions also may contain additives ordinarily found in effervescent formulations. Additives include, but are not limited to, thickeners, surfactants, (emulsifiers), osmotic pressure regulators, electrolytes, sweeteners, flavor enhancers, pigments, pH adjusters, etc. These additives are optionally added to the effervescent formulations of the invention in amounts and proportions known to those of ordinary skill in the art, which would not adversely effect the biological components of the composition.

The effervescent formulations of the invention can include a vitaceutical. A vitaceutical, as used herein, is a vitamin, mineral, antioxidant, or neutraceutical. Vitamins include, but are not limited to, vitamin A, B1, B2, niacin, niacinamide, pentothenic acid-B5, B6, B12, folic acid, biotin, B12, C, D, E, K, and mixtures thereof. Minerals include, but are not limited to, sodium, potassium, magnesium, iodine, molybdenum, manganese, iron, selenium, zinc, calcium, copper, chromium, boron, and vanadium. Antioxidants include, but are not limited to, bioflavanoids, carotenoids, green tea, grape seed extract, pine bark extract, α-lipoic acid, co-enzyme Q10, bilberry, leutin, ginko, garlic, and tumeric.

A nutraceutical, as used herein, is any type of nutrient or pharmaceutical composition. Nutraceuticals include, but are not limited to, glucosamine, glucosamine salts, glucosamine sulfates, hydrochloride, glucosamine carbonate, glucosamine phosphate, methylsulfonylmethane, chondroitin sulfates, ruscus, bromlein, boswellin, carnitine, and salts thereof, hydroxycitric acid, chitosan, acetyl-L-carnitine, phosphatidylserine, huperzine-A, S-adenosylmethione, vinceptine, DMAE, lecithins, ginseng, ashwagandha, ipriflavone, NADH, magnesium malate, d-ribose, herbal extracts such as ginger, fennel seed, St John, kavakava, gugulipids, β-lactam antibiotics, including penicillins, such as amoxycillin or ampicillin, optionally, mixed with a β-lactamase inhibitor; antihistamine $H_2$-receptor antagonists, anti-ulcer compounds such as cimetidine, non-steroidal anti-inflammatories such as aspirin, ibuprofen, naproxen, and nabumetone, and bile acid sequestrants.

Typically, medicaments (including vitaceuticals and nutraceuticals) within the effervescent formulation will comprise approximately 5–50% of the composition weight.

Excipients include, but are not limited to, mannitol, sorbitol, benzoates, propionates, polyethyleneglycol, polyvinyl pyrrolidone, hydrogenated vegetable oils (cotton seed oil, cannola oil, safflower oil, sunflower oil), glycerine and its esters and derivatives, gums, gelatin, propylene, glycol, polysorbates, sucrose esters, lecithin, stearic acid, adipic acid, fumaric acid, lactose, corn starch, talc, crystalline cellulose, mannitol, light silicic anhydride, magnesium carbonate, calcium carbonate, L-cysteine, dextrin, casein, and proteins.

Binders include, but are not limited to, pre-gelatinized starch, methylcellulose, carboxymethylcellulose, polyvinylpyrrolidone, pullulan, and dextrin.

Disintegraters include, but are not limited to, carboxymethylcellulose, calcium, starches, cross-linked carboxymethylcellulose, cross-linked insoluble polyvinylpyrrolidone.

Coloring agents include, but are not limited to, titanium dioxide, beet root powder, riboflavin, red iron oxide, and tar pigment. Fats and oils useful in the effervescent formulations include, but are not limited to, corn oil, peanut oil, essential oil, and vegetable fats and oils.

Clarifying agents include providone, surfactant and anti-foaming agents.

Sweeteners include sugars, saccharine, aspartame, and asulfame K (Hoechst Food Ingredients, Somerset, N.J.).

A surfactant is a wetting agent which is generally ionic and is conventionally used to reduce the surface tension of a liquid. Emulsifiers are wetting agents which are conventionally used as excipients for achieving water-in-oil or oil-in-water emulsions. Emulsifiers include, but are not limited to, sugar esters (e.g. DK-ester$_R$) and polysorbates (e.g. tween), and phospholipids (e.g. lecithins, phosphatidylcholine, metarin, epikuron, phosphatidylethanolamine, phosphatidylinositol, etc. Surfactants include, but are not limited to, docusate sodium, sodium laurylsulphate, etc.

The effervescent formulation is generally dissolved in water prior to ingestion. When effervescent compositions are combined with water, a carbonated or sparkling beverage containing carbon dioxide is formed as a result of the reaction of the acid and base with the water. The amount of water used is usually calculated by determining the amount of organic acid in the effervescent composition which will provide a pH between 4.9 and 5.4 in the final solution.

When the effervescent compositions are prepared, they can be made in the form of a powder or a tablet. To make the powder, the ingredients are mixed under environmental conditions of relative humidity of less than 30%. The powder can then be packaged in pouches or other containers which protect from moisture during storage. Alternatively, the powder can be compressed into tablets and then stored in glass bottles or individually in pouches, again to protect against moisture during storage.

The effervescent compositions are prepared into a tablet form by methods known in the art. For instance, the components are weighed and sized through a screen having a mesh size of approximately 20. The components can then be blended using, for instance, a V blender (PK twin shell). Usually, the taste-masking compositions, clarifying agents, and lubricants are weighed and sized separately and then mixed into the blended ingredients. The final composition is then compressed to produce tablets.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

I claim:

1. An effervescent composition comprising:
   a carbonate or bicarbonate selected from the group consisting of sodium and/or potassium hydrogen carbonates and bicarbonates, calcium carbonate, magnesium carbonate, and amino acid carbonates; at least one pH neutralizing agent selected from the group consisting of L-tartaric acid, citric acid, lactic acid, malic acid, fumaric acid, aspartic acid, ascorbic acid, and amino acids; and an inulin.

2. The effervescent composition of claim 1, further comprising a vitaceutical.

3. The effervescent composition of claim 2, wherein the vitaceutical is a vitamin.

4. The effervescent composition of claim 2, wherein the vitaceutical is a mineral.

5. The effervescent composition of claim 2, wherein the vitaceutical is an antioxidant.

6. The effervescent composition of claim 2, wherein the vitaceutical is a nutraceutical.

7. The effervescent composition of claim 1, wherein the carbonate or bicarbonate is magnesium carbonate and wherein the pH neutralizing agent is malic acid, and wherein the effervescent composition produces magnesium malate in situ.

8. The effervescent composition of claim 7, further comprising glucosamine.

9. The effervescent composition of claim 1, further comprising at least one sweetener, wherein the sweetener is selected from the group consisting of stevia, fructose, ribose, sucrose, tagatose, sucralose, malitol, erythritol, zylitol, acesulfame potassium, aspartame, and saccharine.

10. The effervescent composition of claim 1, further comprising an excipient.

11. The effervescent composition of claim 1, further comprising a surfactant.

12. The effervescent composition of claim 1, further comprising an emulsifier.

13. The effervescent composition of claim 1, further comprising an osmotic pressure-regulator.

14. The effervescent composition of claim 1, further comprising an electrolyte.

15. The effervescent composition of claim 1, wherein the carbonate or bicarbonate is calcium carbonate and wherein the pH neutralizing agent is citric acid and wherein the effervescent composition produces calcium citrate in situ.

16. The effervescent composition of claim 1, wherein the carbonate or bicarbonate is a carbonate of sodium and potassium and the pH neutralizing agent is citric acid.

17. The effervescent composition of claim 3, wherein the nutraceutical is magnesium malate.

18. The effervescent composition of claim 2, wherein the vitaceutical is a vitamin selected from the group consisting of riboflavin-5-phosphate, calcium pentothenate, and peroxidine.

19. The effervescent composition of claim 2, wherein the vitaceutical is a mineral selected from the group consisting of boron chelate, copper gluconate, manganese gluconate, and zinc sulfate.

20. The effervescent composition of claim 2, wherein the vitaceutical is an antioxidant selected from the group consisting of ascorbic acid and vitamin E.

21. A method for treating muscle soreness, comprising, administering to a subject an effervescent composition of claim 4, which produces magnesium malate in situ, in order to treat muscle soreness in a subject.

22. A method for treating osteoporosis, comprising, administering to a subject an effervescent composition of claim 15, which produces calcium citrate in situ, in order to treat osteoporosis in a subject.

23. An effervescent composition comprising:

a basic effervescent agent;

at least one pH neutralizing agent; and glucosamine.

24. The effervescent composition of claim 23 further comprising inulin.

25. The effervescent composition of claim 23 further comprising a vitaceutical.

26. The effervescent composition of claims 23, further comprising chondroitin sulfate.

27. The effervescent composition of claims 23, further comprising methylsulfonylmethane.

28. The effervescent composition of claims 23, further comprising co-enzyme Q10.

* * * * *